(12) United States Patent
Hernández

(10) Patent No.: US 7,972,862 B2
(45) Date of Patent: Jul. 5, 2011

(54) NONINVASIVE GLUCOSE MONITOR

(75) Inventor: Florencio E. Hernández, Orlando, FL (US)

(73) Assignee: The University of Central Florida Research Foundation, Inc., Orlando, FL (US)

( * ) Notice: Subject to any disclaimer, the term of this patent is extended or adjusted under 35 U.S.C. 154(b) by 973 days.

(21) Appl. No.: 11/843,247

(22) Filed: Aug. 22, 2007

(65) Prior Publication Data

US 2008/0058627 A1 Mar. 6, 2008

Related U.S. Application Data

(60) Provisional application No. 60/839,757, filed on Aug. 24, 2006.

(51) Int. Cl.
*G01N 33/00* (2006.01)
(52) U.S. Cl. ............... 436/95; 436/14; 436/80; 436/73; 436/164; 422/82.05
(58) Field of Classification Search .............. 436/14, 436/80, 73, 164, 95; 422/82.05
See application file for complete search history.

(56) References Cited

U.S. PATENT DOCUMENTS 6,975,892 B2 * 12/2005 Burd et al. .................... 600/319

OTHER PUBLICATIONS

Wu et al., "Gold colloid-bienzyme conjugates for glucose detection utilizing surface-enhanced Raman scattering", Talanta 70 (2006) 533-539.*
Zayats et al., "Biocatalytic Growth of Au Nanoparticles: From Mechanistic Aspects to Biosensors Design," Nano Letters, vol. 5, No. 1, pp. 21-25 (2005).
Lewis et al., "Tear Glucose in Diabetics," Brit. J. Ophthal. 42, 754 (1958).
Khalil, "Noninvasive Photonic-Crystal Material for Sensing Glucose in Tears," Clinical Chemistry, 50, No. 12 (2004).
Alexeev et al., "Photonic Crystal Glucose-Sensing Material for Noninvasive Monitoring of Glucose in Tear Fluid," Clinical Chemistry, 50:12, pp. 2353-2360 (2004).
Cho et al., "Non9nvasive Measurement of Glucose by Metabolic Heat Conformation Method," Clinical Chemistry, 50:10, pp. 1894-1898 (2004).
Ko et al., "Body Metabolism Provides a Foundation for Noninvasive Blood Glucose Monitoring," Diabetes Care, vol. 27, No. 5, pp. 1211-1212 (2004).
Weitgasser, et al., "Newer Portable Glucose Meters—Analytical Improvement Compared with Previous Generation Devices?" Clinical Chemistry, 45:10, pp. 1821-1825 (1999).
MacKenzie et al., "Advances in Photoacoustic Noninvasive Glucose Testing," Clinical Chemistry, 45:9, pp. 1587-1595 (1999).
Diabetes in Control Dot Com: J Assoc Phy Ind, 101, 481-483 (2003).
XL, et al., "A glucose biosensor based on chitosan-glucose oxid gold nanoparticles biocomposite formed by one-step electrodeposition," Anal Biochem. 334(2); 284-9 (ISSN: 0003-2697) (2004).
http://pubs.acs.org/cen/news/84/i14/8414glucose.html; Arnaud, "Noninvasive Glucose Detection," Chemical & Engineering News, (2006).
http://www.bioscience.org/2005/v10/af/1599/3.htm; Zhao et al., "Extended-Range Glucose Biosensor Via Layer-By-Layer Assembly Incorporating Gold Nanoparticles," Frontiers in Bioscience 10, 1060-1069 (2005).

* cited by examiner

*Primary Examiner* — Jill Warden
*Assistant Examiner* — Monique Cole
(74) *Attorney, Agent, or Firm* — Jetter & Associates, P.A.

(57) ABSTRACT

A method of sensing glucose in subjects includes the steps of providing a sensing solution including a plurality of metal ions, introducing a bodily fluid sample from a subject into the sensing solution. An optically-based measurable derived from directing incident light on the solution is generated. The concentration of glucose in the bodily fluid using the measurable is then determined which permits the blood glucose level to be derived.

23 Claims, 3 Drawing Sheets

NONINVASIVE GLUCOSE MONITOR

CROSS-REFERENCE TO RELATED APPLICATIONS

The present application claims priority to U.S. Provisional Patent Application Ser. No. 60/839,757 filed Aug. 24, 2006, entitled "NONINVASIVE GLUCOSE MONITOR".

FIELD OF THE INVENTION

The invention is related to glucose monitors.

BACKGROUND OF THE INVENTION

Diabetes mellitus is a medical disorder characterized by persistent variable hyperglycemia (high blood sugar levels), resulting either from inadequate secretion of the hormone insulin, an inadequate response by the body's cells to insulin, or a combination of both of these factors. The most common forms of diabetes are type 1, type 2 and gestational diabetes.

Diabetes is a disease that causes many complications in human normal function. As a result, the amount of glucose in the blood increases while the cells are starved of energy. Over the years, high blood glucose damages nerves and blood vessels, leading to complications such as blindness, heart and kidney disease, nerve problems, gum infections, and amputation.

People with diabetes experiences symptoms such as feeling tired, losing weight, feeling hungry or thirsty, urinating frequently or having vision problems. Symptoms can appear after 10 years or more living with the disease.

This disease also represents the sixth-leading cause of death in USA. Prevention of diabetes-related complications can be accomplished through tight control of glucose levels in the blood. In the last decades many different glucose sensors have been developed. For example, existing glucose sensors and methods include near infrared spectroscopy, optical rotation, enzymatic assays, fluorescence detection, a glucose sensing contact lenses, a biochemical catalyzed reaction embodied as a Continuous Glucose Monitor System (CGMS), and a product called GLUCOWATCH®. However, none of these sensors is fully non-invasive.

The Continuous Glucose Monitoring System (Medtronic MiniMed, Northridge, Calif.) and the GLUCOWATCH® G2 Biographer (Cygnus, Inc., Redwood City, Calif.) are reviewed below. These two devices, each approved by the FDA, measure a signal that is reportedly proportional to blood glucose.

The first device for reading blood glucose levels continuously was approved by the U.S. Food and Drug Administration in June 1999. This device was the Continuous Glucose Monitor System (CGMS) manufactured by Medtronic MiniMed. The CGMS measures interstitial fluid glucose continuously. It calculates and stores a reading every five minutes over a 72-hour period. The CGMS does not provide the glucose results in real time, but rather downloads the readings after they have been collected, the way a 24-hour cardiac holter monitor provides information about cardiac rhythms after they have occurred.

The CGMS contains a wire with a supply of glucose oxidase at the tip, which is inserted subcutaneously into the anterior abdominal wall. This same enzyme is used in many portable blood glucose monitors. Glucose oxidase catalyses a biochemical reaction in the presence of glucose and Oxygen that transfers electrons to a receiving molecule and creates an electronic current, whose magnitude can be measured and converted into a glucose concentration. After 72 hours of measurements, the device is removed and plugged into a docking station to download its readings.

The docking station can be connected to a computer that contains dedicated software for use with the system. The computer will then print out a graph of the three days' blood glucose readings. The CGMS must be recalibrated with a fingerstick blood glucose reading at least four times per day.

The GLUCOWATCH G2 Biographer is worn attached to the wrist, forearm or arm, like a wristwatch. The device measures blood glucose in real time with new readings displayed every 10 minutes and a trend arrow to indicate whether the blood glucose level is rising or falling. Both of these continuous monitors measure the glucose concentration within interstitial fluid glucose.

The GLUCOWATCH® G2 Biographer contains two electrodes, which pull salt from the skin, the salt carries water, and the water carries glucose. The glucose solution, which is a form of diluted interstitial fluid, is collected into a pad called an Autosensor. The Autosensor component of the GLUCOWATCH® G2 Biographer must be replaced after 13 hours of readings are made. The glucose concentration is determined by an electrochemical reaction in the Autosensor. A calculation of the blood glucose level is made every ten minutes. A glucose reading is displayed on the watch face every twenty minutes.

As described above, both the CGMS and GLUCOWATCH® are invasive. Even a contact lens for monitoring glucose is somewhat invasive, besides being uncomfortable. What is needed is a portable, low cost, truly noninvasive glucose sensor that provides high sensitivity and no discomfort to the patient.

SUMMARY

A non-invasive method of sensing glucose in subjects includes the steps of providing a sensing solution including a metal ion from a metal salt, introducing a controlled amount of a bodily fluid sample from a subject into the sensing solution generating an optically-based parameter derived from directing incident light on the solution, and determining the presence of and/or the concentration of glucose in the bodily fluid using the parameter. The optical parameter can be observed by absorbance, reflection, scattering or transmission of light, which can be generated in the form of spectra. The light can be in the visible range or outside of the visible range of the electromagnetic spectrum. Tears can be used as the bodily fluid. The method can include a step of converting the concentration of glucose in the bodily fluid into a concentration of glucose in the blood of the subject by the known relationship between the concentration of glucose in the fluid relative to the concentration of glucose in the blood. The metal salt can be a gold salt. The sensing solution can contain a promoter such as ammonium hydroxide. When the sensing solution includes metal nanoparticles, preferably the nanoparticles have an aspect ratio of 1.1 to 2.0 and more preferably have an aspect ratio of 1.2 to 1.8. These anisotropic metal nanoparticles can be gold nanorods or nanoplates. The sensing solution can be heated to a temperature of 50° C. to 100° C.

A non-invasive glucose monitoring system includes a means of drawing a sample of a body fluid without invasion of body tissue, a sample cell, a sensing solution of a metal salt for placing in the sample cell with the aliquot of the body fluid, a spectrophotometer including: a housing, a sample cell holder for receiving the sample cell, a light source, the light source providing light which irradiates a solution contained in the sample cell, a photodetector for receiving light from the sample cell, and a microprocessor having stored software for determining glucose concentration in blood from spectroscopic data communicably connected to the detector, such that the microprocessor determines the glucose concentration from spectroscopic data provided by the detector, and a power supply, and instructions for use of the system. The power supply can be a battery. A preferred metal salt is a gold salt. The sensing solution can also include a promoter such as ammonium hydroxide. The sensing solution an also include metal nanoparticles that preferably have an aspect ratio of 1.1 to 2.0 and more preferably have an aspect ratio of 1.2 to 1.8. The metal nanoparticles can be nanospheres, nanorods or nanoplates. The spectrophotometer can include a heater and can include a visual or audible alarm if the measured level of glucose is a level that would be a danger for the subject providing the sample. The sensing solution can be provided in a sealed sample cell which can be plastic. The system can also include a lachrymator so that the subject can produce tears on demand.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1:
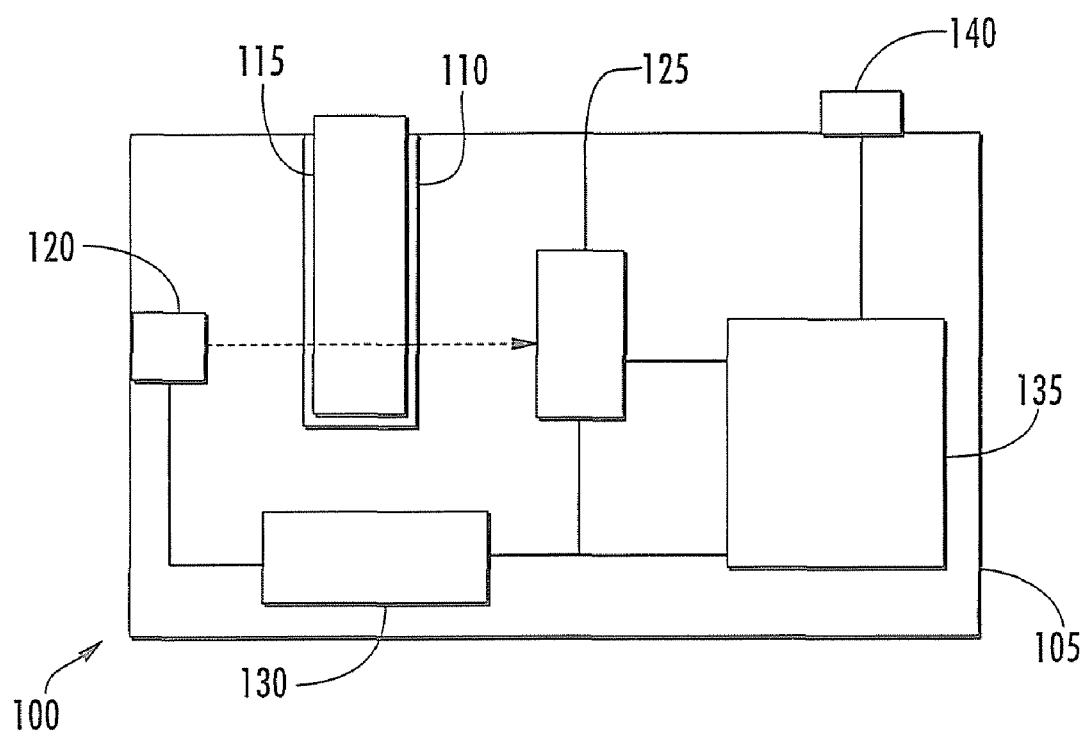
FIG. 1 shows an exemplary noninvasive glucose detector system according to an embodiment of the invention.

A truly non-invasive method of sensing glucose comprises the steps of providing a sensing solution including a plurality of metal ions, and contacting a bodily fluid sample with the sensing solution. The bodily fluid sample is preferably tears. Metal nanoparticles are either formed (hereafter the "nucleation method") or grown on metal seeds from metal ions in the sensing solution (hereafter the "seeding method") in the presence of glucose. A variety of metal ions can be used with the invention, including, but not limited to Au, Ag, Cu, Pd and Pt ions, where these metal ions can be readily reduced to the metallic state. Au has been found to undergo the desired reduction. The concentration of glucose in the body fluid is then determined which allows determination of the blood glucose concentration, if desired.

First, an optical method generates a parameter based on a change in at least one of absorption, reflectance and scattering of the metal nanoparticles resulting from the contacting step. In one embodiment of the reaction, absorption measurements are used. In the nucleation method, higher absorbance corresponds to higher glucose levels. In the seeding method, the magnitude of the red shift in the peak of the longitudinal absorption band is related to the glucose concentration. In the second step the optical parameter is correlated with glucose concentration in the fluid. The glucose concentration in the fluid can then be converted into a glucose level in the blood of the subject.

A full visible light spectrum can be used for analysis. However, useful information can be obtained by performing measurements in a wavelength range of 10 nm, or less, such as centered at around 560 nm for gold.

In one embodiment of the invention ("nucleation method"), metal nanoparticles are nucleated in the solution upon reduction of metal ions when glucose is present in the sample. As the glucose concentration increases, it has been found that the number of nanoparticles increases, while the average size of the nanoparticles remains essentially the same. This allows the concentration of glucose in the body fluid to be determined using a spectroscopic method using the relationship given by the Beer-Lambert law. The concentration of nanoparticles is related to the measured absorbance via a single extinction coefficient for the uniform sized metal nanoparticles formed by the reduction of a dissolved metal salt to the metal particles. The relationship between the concentration of the nanoparticles and the glucose is inherent in the reaction stoichiometry when the average size of the particles is constant as in this nucleation method.

The extinction coefficient of the nanoparticle is ($\epsilon$) related to the absorbance (A) as follows:

$$\epsilon = A/cl$$

where c is the concentration of nanoparticles and l is the path length of the sample. A linear relation has been found by the present Inventor between the absorbance and the glucose concentration for glucose concentrations as low as about 5 mM using a gold salt at a wavelength of around 560 nm to give a constant average size gold nanoparticle as in the nucleation method (see Example 3 below). The concentration of the glucose in the spectrophotometry sample can be related to the body fluid sample by the volume of body fluid introduced to the sample. The relationship of glucose in the body fluid used can be converted to the concentration of glucose in the blood where the concentration profile for glucose in the body sample has been correlated to the profile of blood glucose levels.

In another embodiment of the invention ("seeding method"), a plurality of anisotropic metal (e.g. gold) nanoparticles is provided in the sensing solution along with the plurality of metal ions. The sensing solution is then contacted with a bodily fluid sample. In the presence of glucose, the seeded particles grow in size with a change in the aspect ratio (AR) of the seed particles which results in a red shift in the peak of the longitudinal absorption band. Higher glucose concentrations have been found to result in larger red shifts. The shift can then be correlated with the glucose concentration as in this case the change in the size of the metal nanoparticles is related through the glucose concentration by the reaction stoichiometry. Again the concentration in the body fluid can be calculated for a given volume of the body fluid added to the sample.

Nanoparticle seeds can be obtained from a variety of sources, including commercial sources. As used herein, anisotropic seeds have particle shapes other than spherical displaying an aspect ratio (AR) of at least 1.1. It has been found that the higher the AR (e.g. length/diameter for a nanorod, or the area to thickness ratio for a nanoplate) of the nanoparticles, the better the dynamic range. However, for AR generally greater than about 2, sensitivity is reduced. Accordingly, ARs are preferably in the range from 1.2 to 2.0, more preferably between 1.4 and 1.8 and most preferably about 1.6.

In one embodiment of the seeding method, the metal nanoparticles include surfactant along at least a portion of their length. The surfactant present is generally associated with certain methods that can be used to form the nanoparticles. The metal nanoparticles formed in the presence of surfactant are believed to display greater measurement sensitivity.

In another embodiment essentially spherical seeds, nanospheres can be used and analysis upon measuring the absorption as described above for the "nucleating method".

Although nanospheres can be used with a diameter of 1 to 250 nm or even greater, the extinction coefficient can not generally be treated as a constant for particles in excess of about 50 nm, and corrections are generally included in the calculation of concentration of glucose. Nanosphere seeds having diameters of 5 to 50 nm can be used, such as diameters of 5 to 10 nm or diameters of about 5 nm.

In the nucleation method a surfactant may also be added to the sensing solution. Certain surfactants referred to as coordinating surfactants can be used to control the shape of the nanoparticles formed, such as to form shapes other than generally spherical particles which have been found to form in the absence of a surfactant.

Body fluids in which glucose is found is known to include blood, saliva, urine and tears. Thus, a variety of body fluids can be used with the invention. However, the glucose concentration in tears correlates well with the blood glucose concentration. Accordingly, in an embodiment of the invention the body fluid is tears. Moreover, tears include a minimum of potentially interfering materials found in other body fluids such as saliva. It is believed that a couple of tears will be more than enough to provide a sufficient body fluid volume to determine the glucose concentration. The volume of tears necessary will depend on the glucose concentration in the tears, so diabetics potentially need smaller tear samples than non-diabetics need. It may be necessary in some applications to induce a subject to cry, such as by using onions or other lachrymators to induce tearing.

Although not needed to practice the present invention and not seeking to be bound to the theory presented, reaction details follow that are believed to be operable. The operable generalized reaction utilized by the invention is a redox reaction where glucose functions as the reducing agent according to the following (only reduction product shown):

1. (nucleation method) metal salt+glucose→metal nanoparticles form.
2. (seeding method) metal salt+glucose+anisotropic metal nanoparticle seeds→metal nanoparticles grow and the AR of the nanoparticles change due to the growth.

The above reactions are believed to be made possible based on the equilibrium of glucose in solution between the open-chain aldehyde alcohol form and the cyclic hemiacetal form as shown in schematic (1) below. The presence of the aldehyde can be detected through a reaction with chloroauric acid in aqueous solution, in a manner similar to the Tollen's silver mirror test for aldehydes shown as (2) below.

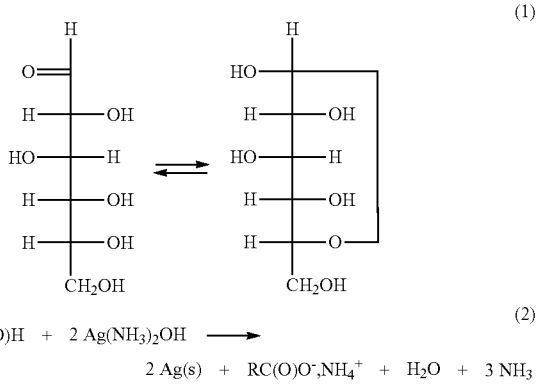

(1)

$RC(O)H + 2 Ag(NH_3)_2OH \longrightarrow$ $2 Ag(s) + RC(O)O^-,NH_4^+ + H_2O + 3 NH_3$ (2)

In the presence of a gluconic acid salt, which is believed to stabilize metal nanoparticles, nanospheres form in the nucleation method or grow in the seeding method during the oxidation of glucose. Gluconic acid is the carboxylic acid forms by the oxidation of the first carbon of glucose and has the chemical formula $C_6H_{12}O_7$. In the nucleation method as more nanospheres form, absorption at the wave length of 560 nm changes proportionally to the glucose concentration. In the seeding method, as the AR of the nanoparticles change, a resulting red shift of the wavelength of the peak absorption can be directly correlated to the amount of glucose oxidized. In either method, the absorbance spectrum (or portion thereof) can be measured using a UV-Vis spectrometer, which can be as small as a cigarette box, or even smaller.

Thus, as shown above, the open chain aldehyde form of glucose acts as a reducing agent and reacts with a metal salt to form metal nanoparticles in the nucleation method or modify the AR in the seeding method. An above ambient temperature, such as about 50 to about 100° C. can be used to increase the reaction rate.

Results obtained using silver salts for the nucleation method have provided useful results. However, gold salts were found to provide much better results. An exemplary reaction for an exemplary gold salt is shown below. The reaction product is gold nanoparticles (nanospheres (NS) absent surfactant addition) shown in reaction (3) below:

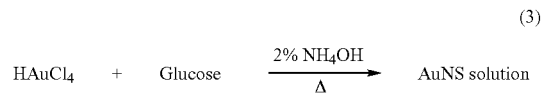

(3)

Heating above room temperature can accelerate of the nanoparticle formation and growth, as noted above, where the solution can be heated, for example to a temperature of 70 to 80° C. Ammonium hydroxide shown above has been found to promote the reaction.

The invention has been found to provide a low limit of detection as is described in the example below for the use of a gold salt. The invention gives highly selective, reliable, and reproducible results and can be embodied in a system that is portable, simple, low cost and noninvasive (no painful testing).

A schematic of an exemplary glucose detector system 100 according to an embodiment of the invention is shown in FIG. 1. System 100 includes a housing 105 having a sample cell holder 110 of appropriate dimensions for insertion of a sample cell 115 such that the proper orientation for the transmission of light from a light source 120 to a photodetector 125, where a light path is shown by a dashed line in FIG. 1, is achieved and the system can be sealed from light external to the housing 105. The sealing of the light can be by any means such as a door, cap, or plug associated with the housing 105, sample cell holder 110 and/or sample cell 115. The sample cell 115 can also be used to store a desired concentration of a metal salt solution for mixture with the prescribed quantity of the body fluid. Although shown as a direct light path in FIG. 1, the system can include mirrors, lenses, and diffraction gratings (not shown) as required to deliver the light as desired to the photodetector 125.

In general, the sample cell 115 can be made from any material of sufficient transparency at the range of wavelengths used for the analysis of the sample. The sample cell 115 can be sufficiently small such that the volume of a single tear can be mixed with a smaller volume of a sensing solution containing a metal salt. The volume of the sample cell can be about 0.1 to about 1 mL or greater. The material for the sample cell 115 can be quartz, glass, or a plastic. Battery 130, such as a lithium ion battery, provides power for the various components of system 100. Microprocessor 135 includes associated memory which stores operating software. Microprocessor 135 is communicably connected to light source 120. Light source 120 provides light which irradiates a solution contained in sample cell 115. Photodetector 125 receives light transmitted through the solution in sample cell 115 and converts the light into an electrical signal. The electrical signal is communicated to microprocessor 135. Microprocessor 135 determines the glucose concentration from data provided by detector 125. The microprocessor 135 can instruct the collection of multiple readings of the optical signal over time such that the complete oxidation of the glucose in the sample can be assured by determining that a maximum signal is reached. Additionally, a means of controlled heating (not shown) of sample cell 115 to a predetermined temperature can be included. In a preferred embodiment, if the glucose concentration is above or below a predetermined concentration, microprocessor commands a light (e.g. blinking red light) or audible alarm 140 to activate. The alarm can also be used to convey other information, such as the viability of the sample for subsequent reuse. Although not shown, system 100 can include a transmitter and antenna to allow data to be monitored at a remote location.

In operation, a user will provide a tear sample and place a predetermined volume of the tear sample into sample cell 115. The specific volume of a sensing solution including a specific concentration of a metal salt can then be added and the components mixed as needed. Alternately, the opposite order of addition of reagents can be carried out. In one embodiment the sample cell 115 is provided with a sealed sensing solution of a specific concentration and volume which has been programmed into the microprocessor such that the sample can be formed upon introduction of a specific volume of the body fluid either through the seal or upon removal of the seal. In another embodiment the sample cell can be used for the collection of a sample of the bodily fluid and a specific portion of the sensing solution of a metal salt can be introduced to the sample cell 115. Sample cell 115 is then inserted into system 100 and the measurement process is begun. The microprocessor can then determine the glucose present in the bodily fluid by performing a differential measurement. Following use, contents of the sample cell 115 can be disposed of, or stored and subsequently reused depending upon the amount of metal salt remaining in the sample cell which can be calculated from the measured optical signal. If reused, an initial optical measurement can be made prior to adding the bodily fluid or the stored previous measurement can be used in the determination of the glucose level. The magnitude of the optical measurement can be used to determine the viability of reusing the sample cell.

Using the glucose measurement, diagnosing diabetes and a variety of other diseases which are associated with an increase or decrease in glucose can be realized. Regarding diabetes, the detection limit is low enough to detect levels of glucose in healthy persons. Using the inventive method, potential diabetic problems can be detected before diabetes has been diagnosed.

EXAMPLES

It should be understood that the Examples described below are provided for illustrative purposes only and do not in any way define the scope of the invention.

Nucleation Embodiment

Figure 2:
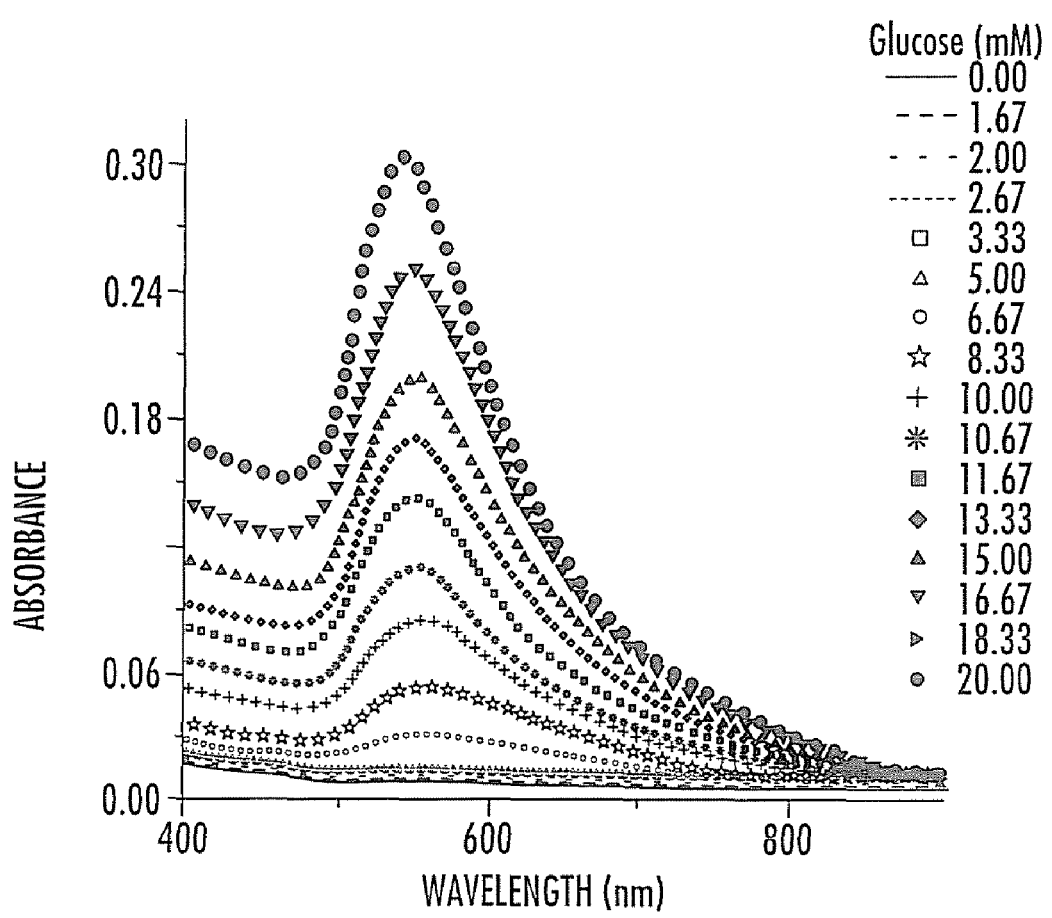
FIG. 2 is a plot showing the absorbance of a sensing solution as a function of wavelength according to an embodiment of the invention in the wavelength range from 400 to 880 nm for a range of glucose concentrations from 0 to 20 mM.

Gold nanospheres were synthesized using a $2.4 \times 10^{-5}$ M chloroauric acid tri-hydrated ($HAuCl_4.3H_2O$) solution, in the presence of various concentrations of glucose in an ammonium hydroxide 2% solution. The concentration of glucose in solution varied from 0 to 20 mM. The reaction was performed at about 70° C. FIG. 2 shows the absorbance of the sensing solution as a function of wavelength in the wavelength range from 400 to 880 nm where glucose was added to achieve solution concentrations from 0 to 20 mM. An absorption peak can be seen at about 560 nm where higher glucose concentrations resulted in higher measured absorbance levels.

Figure 3:
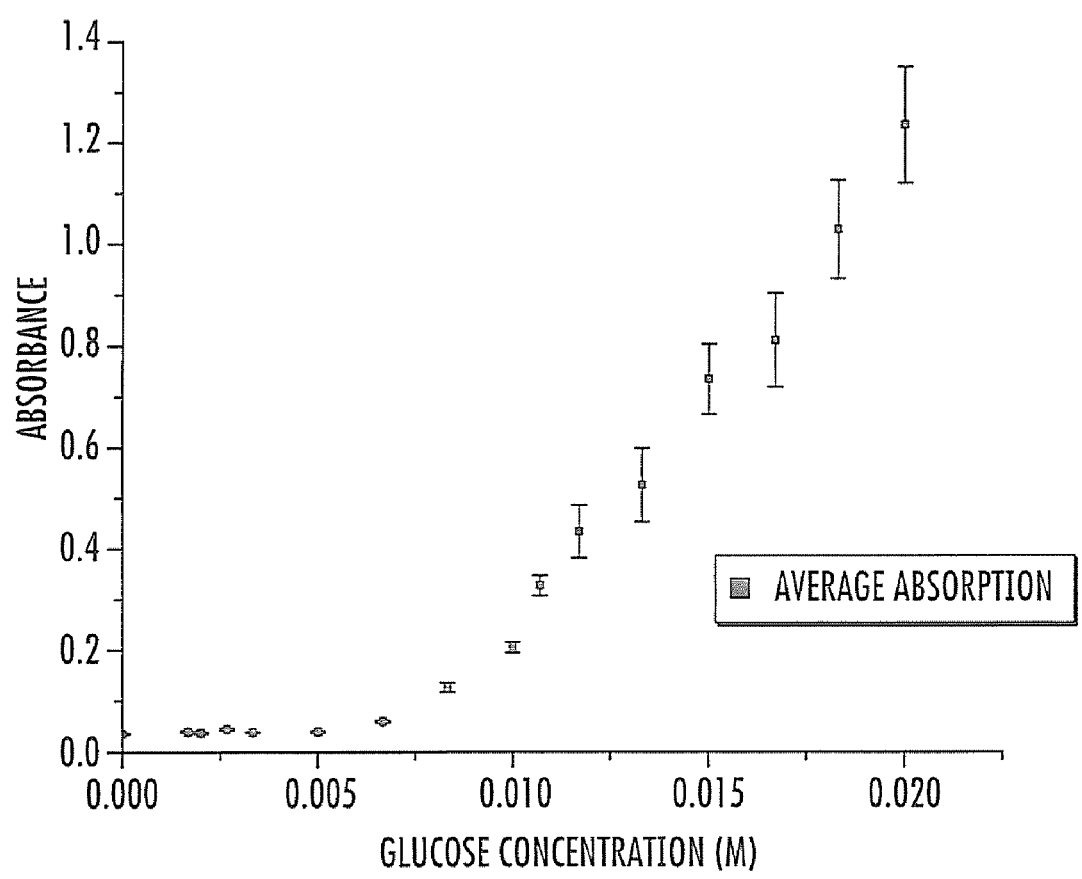
FIG. 3 is a plot showing the absorbance as a function of glucose concentration according to an embodiment of the invention at a wavelength near the gold nanoparticle absorption peak of about 560 nm.

FIG. 3 shows the absorbance dated shown in FIG. 2 at a wavelength near the gold nanoparticle absorption peak of about 560 nm. As shown in FIG. 3, the higher the glucose concentration, from about 6 mM to 20 mM, the higher the value of the absorbance. The relationship is linear. A level of 6.1 mM glucose in the tear is known to correspond to about a 110 mg/dL glucose level in the blood, which is in the normal blood glucose range from 70 to 110 mg/dL. Due to the relationship between the glucose level in tears and the glucose level in blood, the relationship between measured absorbance and blood glucose can be stored, such as in a non-volatile memory in a microprocessor-based system including a spectrophotometer. The measured absorbance provided by a spectrophotometer allows the determination of the blood glucose level by the relationship of the nanoparticle concentration to the glucose concentration from the body sample aliquot and the relationship of the glucose level of a body sample to the blood level. The dependence of the absorbance of the gold nanoparticles solution with glucose concentrations as low as that in common in non-diabetic tears, several mM, makes sensors according to the invention suitable for direct applications in biomedical sensing, including measurements by the subjects themselves.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

I claim:

1. A method of determining glucose concentrations in bodily fluids, comprising:
   providing a sensing solution comprising a plurality of metal ions;
   introducing a bodily fluid sample from a subject into said sensing solution, wherein if glucose is present in said bodily fluid sample said glucose reduces said plurality of metal ions to form metal nanoparticles or increases a size of metal nanoparticle seeds if said metal nanoparticle seeds are also provided in said sensing solution;
   directing incident light at said sensing solution after said introducing;
   measuring at least one optically-based parameter responsive to said directing of said incident light, and
   determining a concentration of said glucose in said bodily fluid sample based on an amplitude of said optically-based parameter wherein a higher absorbance corresponds to a higher glucose concentration or a magnitude of a red wavelength shift of a peak absorption wavelength when said metal nanoparticle seeds are provided in said sensing solution and said optically-based parameter is wavelength, wherein a higher red wavelength shift corresponds to a higher glucose concentration.

2. The method of claim 1, wherein said optically-based parameter comprises absorbance, reflection, scattering or transmission of said incident light.

3. The method of claim 1, wherein said measuring comprises generating a spectrum.

4. The method of claim 1, wherein said bodily fluid sample comprises tear fluid.

5. The method of claim 1, further optionally comprising converting said concentration of glucose into a concentration of glucose in blood of said subject using a correlation relation between a glucose concentration in said bodily fluid sample and glucose concentration in said blood.

6. The method of claim 1, wherein said plurality of metal ions comprise gold ions.

7. The method of claim 1, wherein said sensing solution further comprises a promoter that promotes said glucose reducing said plurality of metal ions.

8. The method of claim 7, wherein said promoter comprises ammonium hydroxide.

9. The method of claim 1, wherein said sensing solution further comprises said metal nanoparticle seeds, said metal nanoparticle seeds comprising a plurality of anisotropic metal nanoparticles, and said optically-based parameter comprises said wavelength shift.

10. The method of claim 9, wherein said plurality of anisotropic metal nanoparticles have an aspect ratio of 1.2 to 1.8.

11. The method of claim 9, wherein said plurality of anisotropic metal nanoparticles comprise gold nanorods or nanoplates.

12. The method of claim 1, further comprising heating said sensing solution to a temperature of 50° C. to 100° C.

13. A glucose monitoring system, comprising:
a sample cell;
a sensing solution comprising a solution comprising a plurality of metal ions in said sample cell together with a bodily fluid sample from a subject, wherein if glucose is present in said bodily fluid sample said glucose reduces said plurality of metal ions to form metal nanoparticles or increases a size of metal nanoparticle seeds if metal nanoparticle seeds are also provided in said sensing solution; and
a spectrophotometer including a light source for measuring at least one optically-based parameter responsive to light from said light source directed at said sample cell, and a microprocessor that includes associated memory for determining a concentration of said glucose in said bodily fluid sample based on an amplitude of said optically-based parameter or a wavelength shift of a peak absorption wavelength when said nanoparticle seeds are provided in said sensing solution and said optically-based parameter is wavelength.

14. The system of claim 13, wherein said plurality of metal ions comprises gold ions.

15. The system of claim 13, wherein said sensing solution further comprising a promoter that promotes said glucose reducing said plurality of metal ions.

16. The system of claim 15, wherein said promoter comprises ammonia hydroxide.

17. The system of claim 13, wherein said sensing solution further comprises said metal nanoparticle seeds, said metal nanoparticle seeds comprising a plurality of anisotropic metal nanoparticles.

18. The system of claim 17, wherein said plurality of anisotropic metal nanoparticles have an aspect ratio of 1.1 to 2.0.

19. The system of claim 17, wherein said plurality of anisotropic metal nanoparticles have an aspect ratio of 1.2 to 1.8.

20. The system method of claim 18, wherein said plurality of anisotropic metal nanoparticles comprise nanospheres, nanorods or nanoplates.

21. The system of claim 13, wherein said spectrophotometer further comprising a visual or audible alarm.

22. The system of claim 13, wherein said sensing solution is provided in a sealed sample cell.

23. The system of claim 13, wherein a correlation relation between glucose concentration in said bodily fluid sample and a glucose concentration in blood is stored in said memory, and wherein said microprocessor converts said concentration of glucose in said bodily fluid sample into a concentration of glucose in blood of said subject.

* * * * *